United States Patent
Deboeck et al.

(10) Patent No.: US 7,858,118 B2
(45) Date of Patent: Dec. 28, 2010

(54) EXTENDED RELEASE COMPOSITION CONTAINING TRAMADOL

(75) Inventors: Arthur M. Deboeck, Gurabo, PR (US); Francis Vanderbist, Meise (BE); Antonio Sereno, Melsbroeck (BE)

(73) Assignee: Galephar Pharmaceutical Research, Inc., Juncos, PR (US)

( * ) Notice: Subject to any disclaimer, the term of this patent is extended or adjusted under 35 U.S.C. 154(b) by 0 days.

(21) Appl. No.: 10/119,939

(22) Filed: Apr. 11, 2002

(65) Prior Publication Data

US 2003/0143270 A1 Jul. 31, 2003

Related U.S. Application Data

(60) Provisional application No. 60/282,858, filed on Apr. 11, 2001.

(51) Int. Cl.
*A61K 9/48* (2006.01)
*A61K 9/20* (2006.01)
*A61K 9/14* (2006.01)

(52) U.S. Cl. ............... 424/456; 424/451; 424/458; 424/459; 424/464; 424/489

(58) Field of Classification Search ............ 424/464, 424/451, 472, 489, 490, 463, 456, 457; 514/356
See application file for complete search history.

(56) References Cited

U.S. PATENT DOCUMENTS

| 5,288,505 | A * | 2/1994 | Deboeck et al. | 424/497 |
| 5,478,577 | A * | 12/1995 | Sackler et al. | 424/489 |
| 5,591,452 | A * | 1/1997 | Miller et al. | 424/468 |
| 5,958,452 | A * | 9/1999 | Oshlack et al. | 424/457 |
| 5,965,161 | A * | 10/1999 | Oshlack et al. | 424/457 |
| 6,156,342 | A * | 12/2000 | Sriwongjanya et al. | 424/473 |
| 6,696,088 | B2 * | 2/2004 | Oshlack et al. | 424/465 |
| 6,806,294 | B2 * | 10/2004 | Wimmer et al. | 514/772.3 |
| 2002/0015730 | A1 * | 2/2002 | Hoffmann et al. | 424/470 |

OTHER PUBLICATIONS

Sorge et al. Comaprison of the analgesic efficacy and tolerability of tramadol 100 mg sustained-release tablets and tramadol 50 mg capsules for the treatment of chronic lower back pain. Clinical Drug Investigation (1997), vol. 14(3), pp. 157-164.*
PCT Written Opinion (PCT Rule 66), PCT/US02/33957, Oct. 24, 2002.
Clinical Drug Investigation, Sep. 1997, vol. 14, No. 3 (pp. 157-245).
Canadian Intellectual Patent Office, Office Action, Oct. 12, 2007.
Canadian Intellectual Patent Office, Office Action, Nov. 6, 2008.
Canadian Intellectual Patent Office, Office Action, Dec. 4, 2009.

* cited by examiner

*Primary Examiner*—Lakshmi S Channavajjala
(74) *Attorney, Agent, or Firm*—William E. Beaumont

(57) ABSTRACT

An oral Tramadol-containing pharmaceutical composition suitable for once daily administration, which contains an amount of Tramadol or a pharmaceutically acceptable salt thereof, providing in vivo, a time of Tramadol peak plasma concentration ($T_{max}$) of greater than 10 hours, and peak Tramadol plasma concentration ($C_{max}$) which are less than three times the plasma concentration obtained 24 hours after administration ($C_{24h}$) of a single dose of the composition.

17 Claims, 2 Drawing Sheets

EXTENDED RELEASE COMPOSITION CONTAINING TRAMADOL

BACKGROUND OF THE INVENTION

1. Field of the Invention

The present invention relates to a once a daily extended release oral Tramadol pharmaceutical preparation which provides effective blood concentration for a period of about 24 hours with reduced peak Tramadol plasma concentrations. The formulation of the present invention provides peak Tramadol plasma concentration s that are less than twice three times the plasma concentration measured 24 hours after administration, while providing for effective Tramadol plasma concentration about 1 to 2 hours after administration.

2. Description of the Background

Tramadol is a centrally acting synthetic analgesic compound that is not derived from natural sources nor is it chemically related to opiates. Although its mode of action is not completely understood, at least two complementary mechanisms appear applicable: Binding to µ-opioid receptors and inhibition of reuptake of nor epinephrine and serotonin. Tramadol opioid activity derives from low affinity binding the parent compound to A-opioid receptors and higher affinity binding of the M1 metabolite. In animal models, M1 is up to 6 times more potent than Tramadol in producing analgesia and 200 times more potent in u-opioid binding. The contribution to human analgesia of Tramadol relative to M1 is unknown.

Tramadol-induced antinociception is only partially antagonized by the opiate antagonist naloxone in animal test. In addition, Tramadol inhibits reuptake of nor-epinephrine and serotonin in-vitro after oral administration of immediate release dosage form the onset of analgesia is evident within 1 hour after administration and reaches a peak in ≈2 to 3 hours. Peak plasma concentrations are reached about 2 hours after administration, which correlates closely with the time to peak pain relief.

Tramadol immediate release is rapidly and almost completely absorbed after oral administration. The mean absolute bioavailability of 100 mg oral dose is ≈75%. Administration with food does not significantly affect its rate or extent of absorption; therefore, it can be administered without regard to meals. The mean peak plasma concentration is 308±78 ng/ml and occurs at ≈2 hours after a single 100 mg oral dose in healthy subjects. At this dose, the mean peak plasma concentration of the active mono-O-desmethyl metabolite (racemic 1) is 55±20 ng/ml and occurs ≈3 hours post-dose. The separate [+]- and [−]-enantiomers of Tramadol generally follow a parallel time course in plasma after a single 100 mg oral dose. Following a 100 mg dose, the maximum plasma concentrations of the [−]-enantiomers are some-what lower than those of the [+]-enatiomer (148±33 vs. 168±36 ng/ml, respectively), The [−]-M1 enantiomer (35±10 vs, 26±13 ng/ml, respectively). Steady state is achieved after 2 days of a 100 mg four times daily dosing regimen (maximum plasma concentration was 592±177 ng/ml). The plasma half-life of Tramadol, following single and multiple dosing, was 6 and 7 hours, respectively. The most common adverse reaction is nausea, vertigo, constipation and headaches and is correlated to the patients plasma Tramadol concentrations.

Tramadol is used for the management of moderate to moderately severe pain such as pain following surgical procedures (orthopedic, gynecological cesarean section) and pain following dental surgery (extraction of impacted molars).

Tramadol ability to control pain is directly related to its concentration in the patient's plasma stream. The minimum effective therapeutical Tramadol plasma level is around 100 ng/ml. Due to Tramadol plasma elimination short half-life to maintain the minimum effective plasma levels requires generally the oral administration of 50 to 100 mg every 4 to 6 hours of immediate release Pharmaceutical compositions. This administration schedule of the drug makes it difficult for the patient to control pain, specially during night time, since pain will reappear every 4 to 6 hours.

On the other hand, if patient in an attempt to control pain for a longer period of time should take higher doses of immediate release Tramadol than peak plasma levels will increase dramatically and very serious side effects due to high blood levels will appear immediately.

Another difficulty encountered by the man skilled in the art for the production of a once daily Tramadol formulation arises from Tramadol extremely high solubility in water and body fluids. The prior art teaching related to Tramadol compositions that may be useful for once daily administration are basically related to maintain effective therapeutically plasma concentrations between administration. Since it is known the therapeutically effective Tramadol plasma levels are close to the unwanted adverse reaction plasma levels, once a day Tramadol compositions to be useful to treat effectively patients in need must not only provide for minimum effective therapeutic plasma levels but also must provide for the control of toxic levels. Any once a day Tramadol formulation which should not comply with both requirements would be useless.

U.S. Pat. No. 5,601,842 discloses a tablet containing Tramadol and a matrixing agent with a viscosity between 3,000 and 150,000 mPa in a 2% aqueous solution at 20° C. U.S. Pat. No. 5,811,126 discloses a controlled release pharmaceutical composition containing Tramadol and comprising sodium alginate, $C_2$ to $C_{50}$, edible hydrocarbon derivative with melting point range from 25° C. to 90° C. and divalent salt to cross link the alginate. In vivo performance from these formulations is not available.

U.S. Pat. Nos. 5,639,476 (12h) and 5,580,578 discloses controlled release dosage form containing a substrate containing Tramadol, said substrate being coated with a plasticized aqueous dispersion of ammonio-methacrylate copolymer having low content of quaterny ammonium groups and a permeability enhancing pore former said coating being cured for about 24 to about 60 hours to stabilize said formulation.

U.S. Pat. No. 5,955,104 discloses a delayed release Tramadol formulation consisting of pellets in a water soluble capsule or in a tablet compressed from said pellets, each pellet having (a) a substantially inert core; (b) an active ingredient layer containing (i) Tramadol particles in mixture with a binder for adhering said Tramadol particles over said inert core, and optionally (iii) a pharmaceutically acceptable, inner adjuvant; and (c) a delay coating for retarding the release of Tramadol consisting principally of mixtures of Ethylcellulose and shellac.

U.S. Pat. Nos. 5,645,858, 5,474,786 and 5,395,626 discloses multilayered controlled release pharmaceutical dosages forms for water soluble drugs comprising a plurality of coated beads and which comprises a core and seven or eight different coatings.

U.S. Pat. No. 5,849,240 describes a process for the manufacture of particles by the "melt-pelletization" process, Tramadol is one of the examples but in vivo performances of such formulation is not available.

US Pat. No. 5,968,551 (continuation of patent 5,273,760) describes sustained release oral analgesic form for once a day administration comprising a unit dose comprising a plurality of pharmaceutical acceptable matrices comprising an analgesically effective amount of Tramadol and hydrophobic material each of said matrices having a diameter of about 0.1 to 3 mm bioavailability and therapeutical effect for about 24 hours or more after oral administration to a human patient (no control of side effects). It also discloses a method of treating patients for moderate to severe pain with a once daily oral administration of a unit dose consisting of a plurality of inert pharmaceutical acceptable beads control with an analgesically effective amount of an opioid analgesic said beads having a diameter of 0.1 to 3 mm and having effective blood levels for about 24 hours (against side effects) with a peak of said opioid in vivo for about 3 to about 10 hours after administration.

U.S. Pat. No. 5,965,163 describes a solid dosage form comprising a plurality of particles including Tramadol in a matrix, the matrix including a mixture of hydrophobic and hydrophilic fusible carriers having melting point from 35° C. to 150° C., which are produced by the method of "melt pelletization".

US Pat. No. 5,591,452 disclosures a once daily Tramadol preparation constituted of Tramadol incorporated into a controlled release matrix constituted of one or more hydrophilic or hydrophobic polymers which provides a $T_{max}$ of about 3 to about 6 hours.

U.S. Pat. No. 5,958,482 describes a sustained release pharmaceutical formulation comprising an extruded blend of Tramadol, and one or more hydrophobic fusible carriers having a melting point from about 300 to about 200° C., providing a sustained-release of said therapeutically active agent for a time period of from about 8 to about 24 hours. With a peak plasma for about 2 to 8 hours.

U.S. Pat. No. 5,891,471 discloses Tramadol pharmaceutical particles for once a day administration which provides a time to peak plasma level of Tramadol in about 2 to about 6 hours after administration, produced by a process of "melt-pelletization".

U.S. Pat. Nos. 5,672,360 and 5,478,577 discloses a method of treating pain in humans comprising orally administering of a once a day basis an oral sustained release dosage form of an opioid analgesic which upon single dose and multiple doses administration provides a time to maximum plasma concentration ($T_{max}$) of said opioid in about 2 to 10 hours and a maximum plasma concentration ($C_{max}$) which is more than twice the plasma level of said opioid at about 24 hours after administration of the dosage form and which dosage form provides effective treatment of pain for about 24 hours or more after administration to the patient.

An orally administrable Tramadol formulation for once a day administration, which would provide effective Tramadol plasma concentrations without Tramadol plasma peaks would be highly desirable.

A pharmaceutical oral dosage formulation of Tramadol a) providing rapidly effective plasma concentration and b) able to maintain such effectives plasma concentration for a long period of time while simultaneously avoiding peak Tramadol blood concentrations would be highly desirable to provide an immediate and extended duration of analgesia with low incidence of adverse effects to patients in pain.

The Tramadol (or salt) once daily composition of the present invention permit the rapid obtention of Tramadol effective plasma concentration, within one or two hours which are maintained for a period of about 24 hours while providing for peak Tramadol blood concentration which are less than free times the concentration obtained twenty four hours after administration.

SUMMARY OF THE INVENTION

OBJECT AND SUMMARY OF THE INVENTION

It is an object of the present invention to provide a once a day oral pharmaceutical preparation of Tramadol or its pharmaceutical acceptable salts.

It is another object of the present invention to provide a once a day Tramadol pharmaceutical preparation which is able to provide effective Tramadol plasma concentration for a period of about 24 hours.

It is another object of the present invention to provide a once daily oral Tramadol preparation which provides effective plasma concentrations within about 1 to 2 hours after single administration of an effective amount of Tramadol for said formulation.

It is another object of the present invention to provide a once a day Tramadol pharmaceutical preparation which effectively reduces the excessive Tramadol plasma concentration.

It is another object of the present invention to provide a Tramadol once a day oral pharmaceutical preparation which after single dose administration to humans provides Tramadol peak plasma concentration ($C_{max}$) less than three times the plasma concentration obtained 24 hours ($C_{24h}$) after said formulation.

It is another object of the present invention to provide a Tramadol once a day oral pharmaceutical preparation which after multiple doses administration to humans provides Tramadol peak plasma concentration ($C_{max}$), which are less man three times the plasma concentration obtained 24 hours ($C_{24h}$) after said multiple administrations.

It is another object of the present invention to provide a Tramadol once a day oral pharmaceutical preparation which after single and/or multiple doses administration to humans provides Tramadol peak concentrations not less than 10 hours ($T_{max}$) after said administration It is another object of the present invention to provide a once daily oral Tramadol pharmaceutical preparation from which the Tramadol rapid rise maximum plasma concentration is lower that the peak concentration of the formulation.

It is another object of the present invention to provide a once a day Tramadol pharmaceutical preparation which is able to control effectively pain during a period of about 24 hours.

It is another object of the present invention to provide a once a day Tramadol preparation which reduces pain within 1 to 2 hours after single administration of an effective amount of Tramadol.

It is another object of the present invention to provide a once daily oral Tramadol pharmaceutical preparation which effectively reduces the unwanted Tramadol side effects due to excessive Tramadol plasma concentration.

It is another object of the present invention to provide a once daily oral Tramadol pharmaceutical preparation which comprise controlled release beads and a tablet into a hard gelatine and/or hydroxypropylmethycellulose capsule.

It is another object of the present invention to provide a once daily oral Tramadol preparation from which the plasma Tramadol concentration are not affected when the formulation is taken with or without food.

It is another object of the present invention to provide a tablet containing Tramadol controlled release beads and a fast release portion of Tramadol constituted by granules, beads or powder which releases the Tramadol in such a manner that the fast releasing Tramadol portion peak plasma concentration is less than the peak concentration obtained from the Tramadol released from the coated beads.

DETAILED DESCRIPTION OF THE PREFERRED EMBODIMENTS

Figure 1:
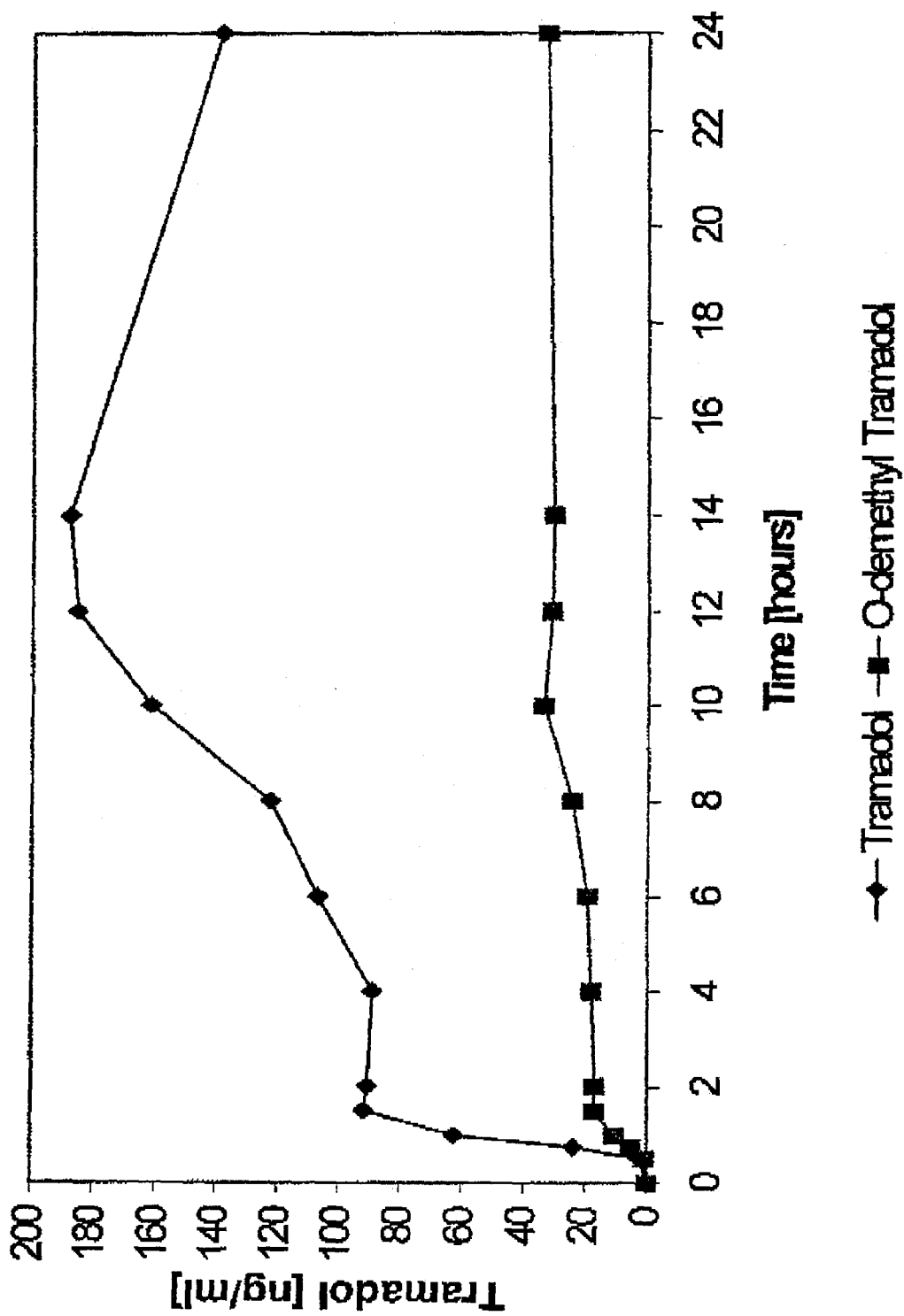
FIG. 1 represent the Tramadol and 0-demethyl Tramadol mean blood concentration obtained after single administration to 8 volunteers of one capsule of example 5 (200 mg) data in Table 1 and 2.
Figure 2:
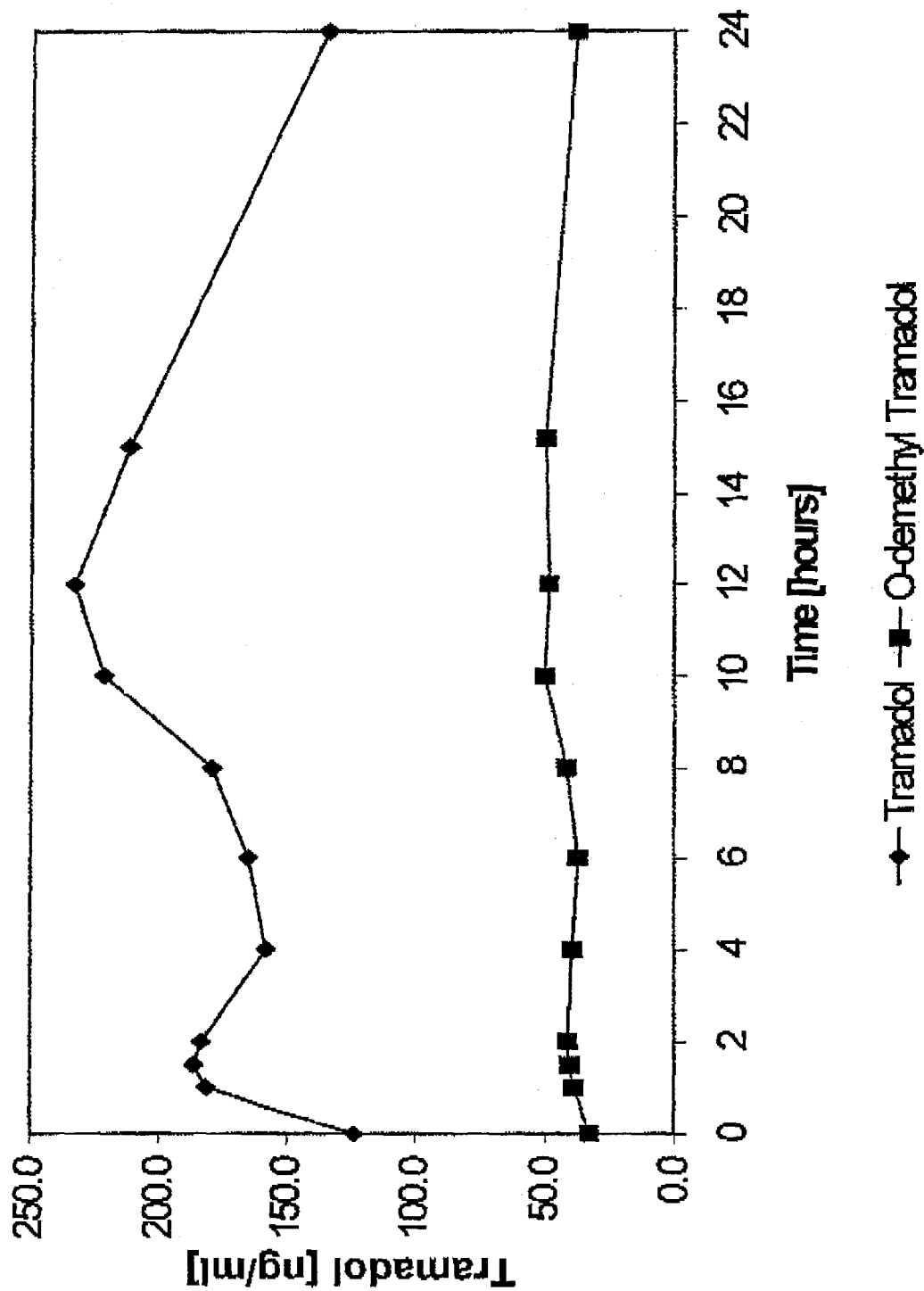
FIG. 2 represent the Tramadol and 0-demethyl Tramadol mean blood concentration obtained after multiple, 7 consecutive, once a day administration to 8 volunteers of one capsule of the product of example 5 containing 200mg of Tramadol (data in Table and 4).

The present invention relate to a novel Tramadol pharmaceutical preparations that provide effective Tramadol plasma concentrations one or two hours after administration and which will be maintained for 24 hours while simultaneously avoiding excessive Tramadol plasma concentrations which are the origin of the unwanted side effects.

More particularly the present invention is related to the discovery, contrary to the teaching of U.S. Pat. Nos. 5,672,360 and 5,478,577 that in order to control pain for about 24 hours, it is necessary that the peak of opioid analgesics concentration ($C_{max}$) is more than twice the concentration obtained 24 hours after administration. In other words, what is disclosed in these patents is the need for large fluctuations of opioid analgesic blood concentrations between successive administration.

More particularly the present invention is related to the discovery that in order to provide for Tramadol peak plasma concentrations that are less than three times the plasma concentration obtained 24 hours after administration it is necessary that the pharmaceutical composition has an in vitro release profile that is not of the first order but rather multiphasic.

More particularly, the present invention relates to a once daily oral pharmaceutical composition comprising a unit dose with at least two Tramadol containing portions who release the Tramadol at different rates. The unit dose may be per example a hard gelatine and/or hydroxypropylmethylcellulose capsule for oral administration.

More particularly, the present invention relate to a unit dose that contains a Tramadol portion who liberate slowly the Tramadol and a Tramadol containing portions that liberates the Tramadol in a faster manner. The unit dose may be a hard capsule and/or a tablet.

In certain preferred embodiments the unit dose comprises a hard gelatine and/or hydroxypropylcellulose capsule containing slow release beads and a fast releasing Tramadol tablet.

In accordance with the present invention any pharmaceutically acceptable salt of Tramadol may be used. In the preferred embodiment the hydrochloride salt of Tramadol may be used.

In another preferred embodiment the unit dose comprises hard gelatine and/or hydroxypropylmethylcellulose capsule containing a slow release tablet and fast releasing beads.

In another preferred embodiment, the unit dose comprises hard gelatine and/or hydroxypropylmethylcellulose capsule containing slow release beads covered by layers of fast release Tramadol.

Bead which are spheroids containing Tramadol or any of its salts may be produced by any conventional known method such as layering the Tramadol in solution with water over a neutral core, or layering over a core the Tramadol in mixture with other pharmaceutical acceptable excipients such as a binders, polymers.

The preferred method for the manufacture of beads in the present invention is the method of extrusion-spheronization. This method comprises mixing the Tramadol or its salts with a spheronizing agent such as microcrystalline cellulose and optionally other pharmaceutical excipients with water.

The blend obtained is thereafter extruded and the extrudate is rounded with the help of a spheronizer.

In a preferred embodiment beads are produced without any binder and comprises a mixture of Tramadol hydrochloride, microcrystalline cellulose and sucrose stearate.

Sustained release bead, are obtained by coating beads, previously manufactured, with a porous membrane from which the Tramadol is liberated slowly, The microporous membrane comprises mixtures of water—soluble and/or water dispersible polymers and/or copolymers and may also include pharmaceutically acceptable adjuvants such as plastifying agents, pigments, fillers, wetting agents, lubricants and anti-foam agents.

Among the water—soluble and/or dispersible film forming polymers or copolymers constituting the microporous membrane, may be mentioned particularly polyacrylates and polymethacrylates of the Eudragit type, such as Eudragit E30D, L30D, RS30 D NE30D of Röhm Pharma (USA), ethylcelluoses, such as Ethocels of DOW, USA and such as AquaCoat of FMC, USA, Hydroxypropyl cellulose and hydroxypropylmethylcellulose and their derivatives.

The polymers or copolymers may be associated into the microporous membrane with at least one adjutant as exemplified by the following: Plastifying agents, such as triacetin, dibutylphthalate, dibutylsebacate, citric acid esters, polyethyleneglycols, polypropyleneglycols and polyvinylpyrrolidone; Pigments such as iron oxides and titanium oxide; fillers, such as lactose and sucrose; Wetting agents, such as surfactive agents of the Span and Tween types, namely partial esters of fatty acids (lauric, palmitic, stearic and oleic acids) and anhydrides of hexitols derived from sorbitol possibly containing polyoxyethylenic chains, preferably surfactive agents of the Tween type, namely Tween 80, as well as polyethyleneglycols; lubricants, such as magnesium stearate and talc; anti-foaming agents, such as silicone oil.

In addition to the polymer or copolymer, the microporous membrane contains preferably, talc and/or magnesium stearate as a lubricant, polyvinylpyrrolidone as a plastifying agent, titanium dioxide as a pigment Tween 80 as a emulsifier, and silicone oil as an antifoaming agent.

Generally, the thickness of the microporous membrane is expressed by the percentage of the dry coating applied onto the uncoated beads.

The weight of the microporous membrane may be 2 to 55%, preferably, 10 to 40%, of the weight of said microganules. These beads may contain the Tramadol or its salt in an amount of 20 to 95% by weight, preferably 30 to 85% by weight. The micorporous membrane may contain 5 to 95% and, preferably, 30 to 50% of polymers, polymer mixture or copolymers.

The microporous membrane for use in the present invention may be applied by coating in equipment such as fluid bed coaters, pan coaters or any suitable coating equipment.

The tablet of the present invention which will be included in the unit dose may be of the fast and/or as sustained release type. In the preferred embodiment fast release tablets are used, The tablets useful for the present invention shall be of such size tat it may be incorporated into the capsule. Tablets having a diameter comprise between 3 and 5 mm are suitable for the present invention. The amount of Tramadol or its salts included into the tablet shall be such that the tablet peak plasma concentration is less than the peak concentration of the beads included in the unit dose. The unit dose Tramadol ratio between the fast release and the sustained release beads is comprised between 1 and 50%, preferably between 5% and 40% and more preferably between 10 and 30%.

The fast release tablets useful for the present invention comprises Tramadol or its salt in mixture with pharmaceutical tabletting agents. The tablets may be produced using conventional tabletting technics.

Sustained release tablets useful for the present invention comprises Tramadol or its salts in combination with retarding agent such as cellulose derivatives, acrylic polymers.

In another embodiment for use in the present invention the sustained release beads coated with the microporous membrane may be covered by layers of a fast release Tramadol. For that purpose, Tramadol or its salts in solution and/or suspension in a solvent is applied onto the coated beads. Adjuvants such as plastifying agents, pigments, fillers, wetting agents lubricants and antifoam agents may also been included. The overcoated Tramadol containing layer may also contain polymer and a copolymers or mixtures thereof to control the release of the fast releasing Tramadol layer.

The following examples illustrate various aspects of the present invention. They are not meat to be constituted to limit the claims in any matter whatsoever.

EXAMPLE 1

Uncoated Beads

| Tramadol Hcl | 31.8 kg |
| Microcrystalline Cellulose (Avicel pH101) | 21.0 kg |
| Sucrose Stearate (Crosdeta F160) | 2.17 kg |
| Purified Water | 7.24 kg |

In a planetary mixer collette of 160 liter capacity introduce the Tramadol Hcl, microcrystalline cellulose and the sucrose stearate, blend at speed 2 for about 15 min. Slowly add the purified water and continue mixing for an additional 15 minutes at speed 2 after all water is added. Extrude the blend through a Fuji Paudal extuder equipped with a 1 mm screen. Spheronize the extrudate during about 2 minutes and dry the beads in an oven at 50° C. for about 12 hours. The died beads are screened though sieves of 1.4 and 0.7 mm. The yields of uncoated beads comprised between 0.7 and 1.4 mm was 44.0 kg (81%).

EXAMPLE 2

Coated Beads

2a. Pre Coating

| Hydroxypropylmethylcelllose | 1.35 kg |
| Talc | 5.40 kg |
| Purified Water | 18.0 kg |

45 kg of sieved beads from Example 1 were placed in an fluidized bed coater (Aeromatic).

The beads were pre coated with 8.25 kg of the coating suspension.

2b. Sustained Release Coating

| Polyacrylate (30%) Eudragit NE30D | 36.7 kg |
| Hydroxypropylmethylcelllose | 1.08 kg |
| Talc | 1.08 kg |
| Polysorbate 80 | 0.216 kg |
| Simethicone | 0.540 kg |
| Magnesium Stearate | 0.216 kg |
| Purified Water | 18.0 kg |

Immediately after the pre coating, 47.8 kg of the sustained release coating was applied onto the pre coated beads. Upon completion of the coating, the coated beads were placed onto trays in a drying oven for about 16 hours at 50° C. Upon cooling the coated beads were stored in containers for further use.

EXAMPLE 3

Tramadol Fast Release Tablet —30 mg

| Tramadol Hcl | 3.00 kg |
| Lactose | 2.63 kg |
| Avicel pH102 | 1.13 kg |
| Povidone | 0.150 kg |
| Starch | 0.525 kg |
| Magnesium Stearate | 0.075 kg |

Introduce a collette planetary mixer with a 20 liter bowl, all ingredients, except the magnesium stearate, ate blend for 15 minutes at speed 2. Add the magnesium stearate and blend for about 1 minute at speed 1. The blend is compressed using dip cup punches of 5 mm diameter to produce 94,000 tablets of 75 mg containing 30 mg of Tramadol Hcl per tablet. The tablets at Example 3 were tested for release of Tramadol using USP Apparatus 1 (Paddles) in 900 mL of a buffer at pH 6.9 at 37° C. and at 50 rotations per minute.

| Time [h] | Tramadol Hcl Dissolved [%] |
| --- | --- |
| 0.25 | 74.5 |
| 0.50 | 98.6 |
| 0.75 | 101.8 |

EXAMPLE 4

Fast Release Tablet — 15 mg

| | |
|---|---|
| Tramadol Hcl | 1.50 kg |
| Manitol | 3.00 kg |
| Povidone XL | 1.73 kg |
| Povidone | 0.20 kg |
| Corn Starch | 1.00 kg |
| Magnesium Stearate | 0.075 kg |

Following the same manufacturing procedure as in Example 4 to produce the blend, 92,000 tables weighting 75 mg and containing 15 mg of Tramadol Hcl per tablet where produced.

EXAMPLE 5

Tramadol Unit Dose

Hard gelatine capsule size #0 where filled with 386.7 mg of beads from Example 2 and one tablet from Example 3 to provide a composition containing 200 mg of Tramadol Hcl per capsule.

A dissoluution test was performed on this composition using USP Apparatus 1 (paddle) at 100 revolution per minute in 900 mL of water at 37° C.

| Time [hours] | Tramadol percent dissolved [%] |
|---|---|
| 1 | 18 |
| 2 | 20 |
| 4 | 24 |
| 6 | 32 |
| 8 | 56 |
| 12 | 67 |
| 16 | 82 |
| 22 | 92 |

As may be seen the dissolution profile is not of the first order type but of the biphasic type.

Single Dose Administration

A single dose of 200 mg of Tramadol Hcl from Example 5 was administered to 8 healthy volunteers and blood concentrations were measured up to 36 hours after administration.

Tramadol Hcl and its metabolite, 0-Desmethyl Tramadol, blood concentrations were measured by LC/MS method. The results axe summarized in Tables 1 and 2.

Multiple Dose Study 200 mg of the composition of example 5 was given once daily during seven days to 8 healthy volunteers. On day 7 the blood concentration were measured during a period of about 35 hours. Tramadol and its metabolite o-demethyl Tramadol blood concentrations were determined using LC/MS analytical method. The results are in Tables 3 and 4.

TABLE 1

Tramadol plasma levels [mg/ml] obtained from 8 healthy volunteers after single administration of Hcl from Example 5 (200 mg).

| Subject | oh | 0.5 | 0.75 | 1 | 1.5 | 2 | 4 | 6 | 8 | 10 |
|---|---|---|---|---|---|---|---|---|---|---|
| 1 | 0 | 1.068 | 57.47 | 61.166 | 72.609 | 89.002 | 45.398 | 67.97 | 61.206 | 64.703 |
| 2 | 0 | 0.734 | 26.894 | 79.184 | 104.18 | 100.95 | 100.42 | 163.46 | 234.15 | 304.35 |
| 3 | 0 | 0.805 | 42.433 | 84.898 | 87.138 | 92.105 | 87.27 | 108.6 | 127.35 | 171.3 |
| 4 | 0 | 1.135 | 24.201 | 134.42 | 111.62 | 116.53 | 76.843 | 75.297 | 96.719 | 134.16 |
| 5 | 0 | 0.384 | 10.726 | 46.362 | 100.12 | 74.449 | 84.478 | 100.68 | 101.3 | 152.23 |
| 6 | 0 | 2.123 | 3.873 | 16.958 | 81.877 | 67.281 | 72.954 | 74.063 | 78.184 | 102.07 |
| 7 | 0 | 0.09 | 0.969 | 19.501 | 71.931 | 101.62 | 124.82 | 148.51 | 148.23 | 197.86 |
| 8 | 0 | 10.165 | 23.982 | 56.001 | 104.14 | 103.35 | 120.33 | 126.33 | 135.05 | 167 |
| MEAN | 0 | 2.1 | 23.8 | 62.3 | 91.7 | 90.7 | 89.1 | 106.9 | 122.8 | 161.7 |
| SD | 0 | 3.3286 | 19.226 | 38.134 | 15.356 | 18.273 | 25.98 | 37.456 | 53.644 | 71.302 |

| Subject | 12 | 14 | 24 | 38 | AUC | Cmax | Tmax | Cmax/C24 |
|---|---|---|---|---|---|---|---|---|
| 1 | 109.06 | 99.172 | 72.374 | 25.313 | 2379.9 | 109.06 | 12 | 1.61 |
| 2 | 327.05 | 346.38 | 201.32 | 75.774 | 7221.3 | 346.38 | 14 | 1.72 |
| 3 | 236.23 | 197.5 | 169.47 | 96.063 | 6288.5 | 236.23 | 12 | 1.39 |
| 4 | 145.45 | 138.37 | 88.493 | 42.295 | 3372.7 | 145.45 | 12 | 1.64 |
| 5 | 144.74 | 159.64 | 140.87 | 57.89 | 4182.7 | 159.84 | 14 | 1.13 |
| 6 | 92.148 | 100.05 | 70.298 | 36.974 | 2567.4 | 102.07 | 10 | 1.45 |
| 7 | 240.27 | 280.23 | 201.99 | 118.39 | 6503.5 | 280.23 | 14 | 1.39 |
| 8 | 196.78 | 180.56 | 166.7 | 62.032 | 4994.2 | 186.76 | 12 | 1.11 |
| MEAN | 185.2 | 187.7 | 139.2 | 64.3 | 4563.8 | 196.73 | 12.5 | 1.42 |
| SD | 78.771 | 86.709 | 65.257 | 31.311 | 1766.9 | 85.917 | 1.4142 | 0.217 |

TABLE 2

O-demethyl Tramadol plasma levels [mg/ml] obtained from 8 healthy volunteers after single administration of 200 mg of Tramadol from Example 5.

| subjects | 0 | 0.5 | 0.75 | 1 | 1.6 | 2 | 4 | 6 | 8 | 10 | 12 | 14 | 24 | 36 | AUC | Cmax | Tmax | Cmax/C24 |
|---|---|---|---|---|---|---|---|---|---|---|---|---|---|---|---|---|---|---|
| 1 | 0 | 0.1 | 22.3 | 27.3 | 33.8 | 30.4 | 25.8 | 26.8 | 31.1 | 44.2 | 43.1 | 45.8 | 44.1 | 19.6 | 1290.8 | 45.8 | 14 | 1.04 |
| 2 | 0 | 0.0 | 1.6 | 2.1 | 5.3 | 5.7 | 5.7 | 8.1 | 12.1 | 16.4 | 18.0 | 19.5 | 18.1 | 5.8 | 460.67 | 19.5 | 14 | 1.21 |
| 3 | 0 | 0.0 | 4.3 | 7.4 | 9.6 | 11.7 | 11.1 | 14.4 | 18.1 | 27.9 | 34.2 | 28.7 | 23.9 | 17.9 | 777.5 | 34.2 | 12 | 1.43 |
| 4 | 0 | 0.0 | 4.5 | 22.7 | 33.5 | 29.6 | 25.7 | 23.6 | 27.5 | 41.6 | 38.0 | 38.8 | 35.6 | 22.1 | 1121.1 | 41.6 | 10 | 1.17 |

TABLE 2-continued

O-demethyl Tramadol plasma levels [mg/ml] obtained from 8 healthy volunteers after single administration of 200 mg of Tramadol from Example 5.

| subjects | 0 | 0.5 | 0.75 | 1 | 1.6 | 2 | 4 | 6 | 8 | 10 | 12 | 14 | 24 | 36 | AUC | Cmax | Tmax | Cmax/C24 |
|---|---|---|---|---|---|---|---|---|---|---|---|---|---|---|---|---|---|---|
| 5 | 0 | 0.0 | 0.9 | 5.0 | 8.8 | 6.1 | 9.4 | 12.6 | 12.7 | 21.3 | 21.9 | 20.8 | 28.2 | 13.1 | 885.55 | 28.2 | 24 | 1.00 |
| 6 | 0 | 2.2 | 0.4 | 6.4 | 21.5 | 24.9 | 36.2 | 26.7 | 26.7 | 31.3 | 30.9 | 25.6 | 37.7 | 17.6 | 1022.6 | 37.7 | 24 | 1.00 |
| 7 | 0 | 0.0 | 0.0 | 1.5 | 6.3 | 5.3 | 7.0 | 9.5 | 12.1 | 18.5 | 18.5 | 23.8 | 23.7 | 18.0 | 652.47 | 23.8 | 14 | 1.00 |
| 8 | 0 | 3.0 | 6.8 | 11.3 | 16.8 | 19.2 | 22.8 | 33.4 | 55.1 | 69.0 | 43.3 | 42.5 | 53.4 | 25.1 | 1479.8 | 69.0 | 10 | 1.29 |
| MEAN | 0 | 0.7 | 6.0 | 10.6 | 16.9 | 16.8 | 18.0 | 19.4 | 24.4 | 33.8 | 31.0 | 30.4 | 32.9 | 17.4 | 936.3 | 37.6 | 15.3 | 1.14 |
| SD | 0 | 1.20 | 7.32 | 9.86 | 11.65 | 10.55 | 11.15 | 9.38 | 14.56 | 17.48 | 10.46 | 10.04 | 12.23 | 5.85 | 350.02 | 15.5 | 5.7 | 0.160 |

TABLE 3 tramadol levels multiple doses
tramadol plasma concentrations [mg/ml] obtained after 7 consecutive administrations
of 200 mg of tramadol HCl from Example 5 to 8 healthy volunteers

| | time [hours] after the seventh administration | | | | | | | | |
|---|---|---|---|---|---|---|---|---|---|
| subject | −24 | 0 | 1 | 1.5 | 2 | 4 | 6 | 8 | 10 |
| 1 | 162.2 | 187.9 | 230.5 | 239.1 | 271.7 | 210 | 209.0 | 265.5 | 340.5 |
| 2 | 128.6 | 99.5 | 165.7 | 172.3 | 156.1 | 125 | 103.4 | 117.9 | 151.7 |
| 3 | 87.4 | 84.1 | 104.9 | 156.6 | 162.8 | 161 | 157.0 | 160.9 | 200.2 |
| 4 | 49.9 | 62.8 | 170.4 | 130.2 | 135.7 | 114 | 110.4 | 103.6 | 132.0 |
| 5 | 104.1 | 125.9 | 195.1 | 191.5 | 179.0 | 204 | 242.4 | 269.0 | 358.4 |
| 6 | 163.2 | 135.0 | 207.7 | 199.5 | 185.3 | 150 | 189.6 | 163.1 | 176.4 |
| 7 | 187.7 | 193.6 | 238.4 | 244.4 | 224.0 | 176 | 198.0 | 227.9 | 259.8 |
| 8 | 81.7 964.9 | 103.1 | 140.6 | 160.8 | 155.3 | 126 1266 | 133.9 | 131.7 | 155.0 |
| mean | 120.6 | 124.0 | 181.7 | 186.8 | 183.7 | 158.2 | 165.5 | 180.0 | 221.5 |
| SD | 47.8171 | 46.92 | 45.392 | 40.089 | 44.264 | 36.342 | 49.046 | 65.676 | 87.524 |

| | time [hours] after the seventh administration | | | | AUC | | | |
|---|---|---|---|---|---|---|---|---|
| subject | 12 | 16 | 24 | 36 | 0-36 | Cmax | Tmax | Cmax/C24 |
| 1 | 315.0 | 305.8 | 143.7 | 48.9 | 7198.9 | 340.5 | 10 | 2.4 |
| 2 | 177.7 | 161.7 | 110.8 | 32.9 | 4226.1 | 177.7 | 12 | 1.8 |
| 3 | 226.4 | 174.8 | 131.0 | 41.3 | 4997.6 | 226.4 | 12 | 1.7 |
| 4 | 152.0 | 131.2 | 84.6 | 23.2 | 3509.2 | 170.4 | 1 | 2.0 |
| 5 | 322.3 | 287.3 | 161.4 | 37.6 | 7121.8 | 356.4 | 10 | 2.2 |
| 6 | 196.0 | 209.3 | 147.0 | 45.9 | 5437.7 | 209.3 | 15 | 1.4 |
| 7 | 309.7 | 261.7 | 190.3 | 78.3 | 7213.0 | 309.7 | 12 | 1.6 |
| 8 | 163.7 | 163.2 | 113.3 | 38.0 | 4331.6 | 163.7 | 12 | 1.4 |
| mean | 232.8 | 211.9 | 135.3 | 43.2 | 5504.5 | 244.3 | 10.5 | 1.8 |
| SD | 72.13 | 65.15 | 32.914 | 16.2362 | 1495.6 | 79.3 | 4.1 | 0.4 |

TABLE 4

O-desmethyl tramadol levels multiple doses
O-desmethyl tramadol blood concentrations obtained after 7 consecutive administrations
of 200 mg of tramadol HCl from example 5 to 8 healthy volunteers

| | time [hours] after the seventh administration | | | | | | | | |
|---|---|---|---|---|---|---|---|---|---|
| subject | −24 | 0 | 1 | 1.5 | 2 | 4 | 6 | 8 | 10 |
| 1 | 53.8 | 36.1 | 54.3 | 50.3 | 44.6 | 44.1 | 38.4 | 46.1 | 53.9 |
| 2 | 38.1 | 35.5 | 43.9 | 43.4 | 41.8 | 34.9 | 30.6 | 32.3 | 39.0 |
| 3 | 71.3 | 38.6 | 49.8 | 85.0 | 58.5 | 52.9 | 70.9 | 69.0 | 117.1 |
| 4 | 28.0 | 32.4 | 54.8 | 40.5 | 49.5 | 47.1 | 41.3 | 40.8 | 47.2 |
| 5 | 10.1 | 11.0 | 14.5 | 14.4 | 14.5 | 13.8 | 16.7 | 18.7 | 22.8 |
| 6 | 9.2 | 8.4 | 11.4 | 10.8 | 10.0 | 9.1 | 7.8 | 7.5 | 7.5 |
| 7 | 80.9 | 64.1 | 39.6 | 58.9 | 68.2 | 72.2 | 52.5 | 79.0 | 74.3 |
| 8 | 34.2 | 33.7 | 41.5 | 42.0 | 43.9 | 41.5 | 38.6 | 40.8 | 43.2 |
| mean | 40.7 | 32.5 | 38.7 | 40.4 | 41.1 | 39.4 | 37.1 | 41.8 | 50.6 |
| SD | 26.3665 | 17.333 | 16.846 | 19.056 | 19.8 | 20.499 | 19.696 | 23.744 | 33.422 |

TABLE 4-continued

O-desmethyl tramadol levels multiple doses
O-desmethyl tramadol blood concentrations obtained after 7 consecutive administrations
of 200 mg of tramadol HCl from example 5 to 8 healthy volunteers

| subject | time [hours] after the seventh administration | | | | AUC | | | |
|---|---|---|---|---|---|---|---|---|
| | 12 | 15.2 | 24 | 36 | 0-36 | Cmax | Tmax | Cmax/C24 |
| 1 | 56.4 | 43.9 | 29.4 | 10.4 | 1279.3 | 56.4 | 10 | 1.9 |
| 2 | 45.8 | 55.0 | 40.0 | 17.4 | 1369.5 | 55.0 | 15 | 1.4 |
| 3 | 72.6 | 94.5 | 90.4 | 21.6 | 2606.7 | 117.1 | 10 | 1.3 |
| 4 | 49.6 | 53.6 | 31.2 | 12.8 | 1341.7 | 54.6 | 1 | 1.7 |
| 5 | 23.8 | 23.6 | 16.3 | 4.2 | 583.2 | 23.8 | 12 | 1.6 |
| 6 | 9.5 | 11.5 | 9.2 | 2.7 | 300.5 | 11.5 | 16 | 1.2 |
| 7 | 88.5 | 78.4 | 54.8 | 34.8 | 2207.6 | 88.5 | 12 | 1.6 |
| 8 | 44.0 | 42.3 | 33.8 | 13.6 | 1252.8 | 44.0 | 12 | 1.3 |
| mean | 48.9 | 50.3 | 38.1 | 14.7 | 1367.6 | 56.4 | 10.9 | 1.5 |
| SD | 25.06 | 26.98 | 26.269 | 10.2549 | 757.5 | 33.7 | 4.4 | 0.2 |

EXAMPLE 6

Coated Beads 30 kg of beads from Example 1 were coated firs with 5.5 kg of the precoating suspension of Example 2 followed by 36 kg of the sustained release coating of Example 2.

EXAMPLE 7

30 mg Tablets

| | |
|---|---|
| Tramnadol Hcl | 6.00 kg |
| Lactose | 0.72 kg |
| Microcrystalline Cellulose | 1.20 kg |
| Povidone | 0.18 kg |
| Starch | 0.56 kg |
| Sodium Starch Glycolate | 0.24 kg |
| Magnesium Stearate | 0.09 kg |
| Purified Water | 1.00 kg |

Tablets containing 30 mg Tramadol were prepared as per method described in Example 3—using a 160L planetary blend. The tablets weight was 75 mg.

EXAMPLE 8

200 mg Capsules

Hard gelatin capsules Size #0 were fined with one tablet of Example 7 and 341 mg of beads from Example 6 treated with 0.5% of Talc.

A dissolution test was performed on this drug composition using USP apparatus 1 at 100 rpm in 900 ml of water at 37° C.

| Time [h] | Tramadol Percent Dissolved |
|---|---|
| 1 | 28 |
| 7 | 50 |
| 24 | 100 |

EXAMPLE 9

300 mg Capsules

Hard gelatin capsules Size #00 were filled with one tablet of Example 7 and 568 tag of beads from Example 6 treated with 0.5% of Talc.

A dissolution text was performed on this drug composition using the same equipment and parameters as for Example 8.

| Time [h] | Tramadol Percent Dissolved |
|---|---|
| 1 | 21 |
| 8 | 48 |
| 24 | 95 |

As shown by the dissolution results of pharmaceutical preparations of examples 8 and 9, the Tramadol release profile is diphasic.

A single Dose pharmaceutical study was undertaken with formulations of Examples 8 and 9.

Single Tramadol ER capsules containing 200 mg 200 mg and 300 mg were administered in cross over to twenty healthy subjects without food. Blood was monitor and plasma analyzed for Tramadol content up to 72 hours.

Results are summarized in Table 5.

TABLE 5

Tramadol and o-desmethyl-tramadol plasma concentration after single
dose administered to 20 healthy volunteers of 200 mg (Example 8) and
300 mg (Example 9) of Tramadol formulation.

| Time | Tramadol Plasma Level [mg/ml] | | O-demethyl-Tramadol Plasma Level [mg/ml] | |
|---|---|---|---|---|
| [h] | 200 mg | 300 mg | 200 mg | 300 mg |
| 0 | 0.0 | 0.0 | 0.0 | 0.0 |
| 0.5 | 19.20 | 20.4 | 5.5 | 6.5 |
| 1 | 123.7 | 121.6 | 23.2 | 24.2 |
| 1.5 | 158.9 | 156.7 | 32.0 | 32.3 |
| 2 | 168.1 | 159.9 | 35.5 | 35.1 |
| 2.5 | 165.0 | 160.6 | 37.2 | 36.2 |
| 3 | 152.3 | 156.1 | 35.0 | 36.8 |
| 3.5 | 147.9 | 150.0 | 35.0 | 36.3 |

TABLE 5-continued

Tramadol and o-desmethyl-tramadol plasma concentration after single dose administered to 20 healthy volunteers of 200 mg (Example 8) and 300 mg (Example 9) of Tramadol formulation.

| Time | Tramadol Plasma Level [mg/ml] | | O-demethyl-Tramadol Plasma Level [mg/ml] | |
|---|---|---|---|---|
| [h] | 200 mg | 300 mg | 200 mg | 300 mg |
| 4 | 144.5 | 152.2 | 35.3 | 38.2 |
| 5 | 160.7 | 180.9 | 38.7 | 43.2 |
| 6 | 175.2 | 228.0 | 39.9 | 50.1 |
| 8 | 228.1 | 320.8 | 51.8 | 69.6 |
| 10 | 271.6 | 385.8 | 62.4 | 86.4 |
| 11 | 275.6 | 384.3 | 64.1 | 89.7 |
| 12 | 273.9 | 387.8 | 64.7 | 89.7 |
| 13 | 267.2 | 386.3 | 64.9 | 93.1 |
| 14 | 255.7 | 384.9 | 63.4 | 95.0 |
| 15 | 251.1 | 364.0 | 64.9 | 90.8 |
| 16 | 232.0 | 344.0 | 61.7 | 88.8 |
| 17 | 216.7 | 318.0 | 59.8 | 83.9 |
| 18 | 198.7 | 302.2 | 56.1 | 81.4 |
| 20 | 177.4 | 269.7 | 52.6 | 73.1 |
| 24 | 126.9 | 201.0 | 40.2 | 57.5 |
| 36 | 46.6 | 78.6 | 15.8 | 24.5 |
| 48 | 18.5 | 33.0 | 6.4 | 10.6 |
| 72 | 2.6 | 4.4 | 0.8 | 1.5 |
| Ratio $C_{max}/C_{24}$ | 2.2 | 1.9 | 1.6 | 1.7 |
| $T_{max}$ [h] | 11 | 12 | 13-15 | 14 |

The invention claimed is:

1. A solid pharmaceutical composition in a capsule comprising an effective amount of Tramadol or a pharmaceutically acceptable salt thereof, and a pharmaceutically acceptable carrier; the composition comprising a fast release Tramadol tablet, and slow release Tramadol beads, said tablet comprising between 10 and 30% by wt. of a unit dose of Tramadol or salt thereof, and said beads being free of binder and comprising a Tramadol salt, sucrose stearate and being coated with a porous membrane from which the Tramadol is liberated slowly and exhibiting an at least biphasic absorption profile in vivo under fed and fasted administration conditions providing a time of Tramadol peak plasma concentration (Tmax) greater than about 10 hours after administration and peak concentration ($C_{max}$) which is less than about three times the plasma concentration obtained 24 hours after once daily administration ($C_{24th}$) of a single dose of said composition; and wherein a first peak of plasma concentration rise occurs within about 0.5 to 4 hours after administration, and wherein the capsule comprises a gelatine or hydroxypropylmethylcellulose capsule.

2. The pharmaceutical composition of claim 1, which provides, after single administration in vivo, O-desmethyl Tramadol peak plasma concentration ($C_{max}$) which is less than about twice the plasma concentration obtained 24 hours after administration ($C_{24th}$).

3. The pharmaceutical composition of claim 1, which provides, after single administration in vivo, a time of O-desmethyl Tramadol peak plasma concentration ($T_{max}$) greater than about 10 hours.

4. The pharmaceutical composition of claim 1, wherein said pharmaceutical composition provides a pharmacokinetic profile that is unaffected by patient food intake.

5. The pharmaceutical composition of claim 1, wherein said pharmaceutical composition provides effective pain control in humans during a period of about 24 hours after administration.

6. The pharmaceutical composition of claim 5, wherein the pharmaceutical composition provides effective pain control in humans, starting at about 1 to 2 hours after administration and lasting for about 24 hours after administration.

7. The pharmaceutical composition of claim 1, wherein said fast release Tramadol tablet releases about 80% of Tramadol therein within 1 hour.

8. The pharmaceutical composition of claim 1, wherein said beads are free of binder and comprise a mixture of Tramadol hydrochloride, microcrystalline cellulose and sucrose stearate.

9. The pharmaceutical composition of claim 1, wherein the amount of Tramadol or salt thereof in said tablet in such that a peak plasma concentration therefrom is less than a peak plasma concentration from said beads.

10. A method of treating post-surgical pain, which comprises administering an effective amount of the pharmaceutical composition of claim 1, to a mammal in need thereof.

11. The method of claim 10, wherein the mammal is a human.

12. The pharmaceutical composition of claim 1, wherein said porous membrane is a microporous membrane.

13. The pharmaceutical composition of claim 12, wherein said microporous membrane is present in an amount of 2 to 55% by weight of the weight of the beads.

14. The pharmaceutical composition of claim 12, wherein said microporous membrane is made of a water-soluble or dispersible film-forming polymer or copolymer comprising polyacrylates, polymethacrylates, ethylcelluloses, hydroxylpropyleellulose or hydroxypropylmethylcellulose.

15. The pharmaceutical composition of claim 1, which exhibits a biphasic absorption profile in vivo under fed and fasted administration conditions.

16. The pharmaceutical composition of claim 1, wherein said fast release tablet has a diameter of between 3 mm and 5 mm.

17. The pharmaceutical composition of claim 1, wherein a first $C_{max}$ obtained from said fast release tablet is less than a second $C_{max}$ obtained from said slow release beads.

* * * * *